United States Patent [19]

Mittleman et al.

[11] 4,430,077
[45] Feb. 7, 1984

[54] INJECTION SITE WITH TAMPER INDICATOR

[75] Inventors: Herbert Mittleman, Deerfield; William L. Rush, Park Ridge, both of Ill.

[73] Assignee: Baxter Travenol Laboratories, Inc., Deerfield, Ill.

[21] Appl. No.: 392,413

[22] Filed: Jun. 25, 1982

Related U.S. Application Data

[63] Continuation of Ser. No. 195,885, Oct. 10, 1980, abandoned.

[51] Int. Cl.³ .............................................. A61M 5/14
[52] U.S. Cl. ..................................... 604/111; 604/86; 215/249; 215/253; 215/305
[58] Field of Search ............... 215/247, 249, 253, 305; 604/83, 86, 110, 111, 262, 408–410

[56] References Cited

U.S. PATENT DOCUMENTS

| | | | |
|---|---|---|---|
| 2,191,447 | 2/1940 | Beardsley | 604/111 |
| 3,332,418 | 7/1967 | Brody | 604/86 |
| 3,915,212 | 10/1975 | Bujan et al. | 604/408 X |
| 4,048,995 | 9/1977 | Mittleman | 604/86 |
| 4,303,067 | 12/1981 | Connolly et al. | 604/408 |

FOREIGN PATENT DOCUMENTS 591372 9/1977 Switzerland ..................... 215/305

Primary Examiner—Dalton L. Truluck
Attorney, Agent, or Firm—P. C. Flattery; John P. Kibby, Jr.; Bradford R. L. Price

[57] ABSTRACT

A tamper indicating device (24) is connected to the inlet (14) of an injection site (10) which inlet (14) includes a pierceable, self-sealing member (16). The tamper indicating device (24) comprises a cap (26, 28) which covers the inlet (14) rendering the pierceable, self-sealing member (16) inaccessible. A first portion (26) of the cap is connected to the inlet (14) and a second portion (28) of the cap is separated from the first portion (26) by a frangible section (30). A handle (32) extends from the second portion (28) and is operable when actuated to break the second portion (28) away from the first portion (26) at the frangible section (30), rendering the pierceable, self-sealing member (16) accessible. The first portion (26) remains connected to the inlet (14) to indicate that tampering has occurred.

3 Claims, 6 Drawing Figures

INJECTION SITE WITH TAMPER INDICATOR

This application is a continuation of U.S. patent application Ser. No. 195,885, filed Oct. 10, 1980 now abandoned.

TECHNICAL FIELD

The present invention concerns an injection site which carries a device for indicating that an injection has occurred or that the injection site has been tampered with.

BACKGROUND ART

Injection sites are commonly used in hospitals where a parenteral fluid is being fed to a patient intravenously and it is also desired to combine another medicament with the parenteral fluid. In such circumstances, the parenteral fluid is fed via flexible conduit to one inlet of a connecting device, commonly called an injection site. Flexible conduit extends from the outlet of the injection site to an appropriate device for administering the liquid to the patient. The injection site typically has a second inlet, having a pierceable diaphragm connected thereto. The supplementary medicament is injected into the second inlet by a hypodermic syringe and it becomes combined with the parenteral liquid for administration to the patient. A type of injection site which comprises the above-described characteristics is disclosed in Herbert Mittleman U.S. Pat. No. 4,00,740, issued Jan. 4, 1977, and entitled "Injection Site".

The pierceable diaphragm is formed of a self-sealable material, such as Latex or silicone rubber, and it is often impossible to determine whether an injection has been made into the diaphragm by merely viewing it. In addition, since prior art injection sites generally utilize pierceable diaphragms which are exposed to ambient surroundings, it is possible for the pierceable diaphragm to have come in contact with various fluid contaminants without anyone knowing whether such has occurred. Further, if the injection site is not stored properly, a layer of dust may collect upon the pierceable diaphragm.

DISCLOSURE OF THE INVENTION

It is an object of the present invention to provide means for determining whether injection into the pierceable diaphragm has occurred or whether tampering has occurred.

Another object of the present invention is to provide tamper indicating means for an injection site, which also serves to prevent the pierceable diaphragm of the injection site from being contaminated with dust or certain gross contaminants.

Another object of the present invention is to provide an injection site including tamper indicating means that is simple in construction and efficient to manufacture.

A still further object of the present invention is to provide tamper indicating means for an injection site, which renders the pierceable diaphragm inaccessible until a portion of the tamper indicating means is removed.

Other objects and advantages of the present invention will become apparent as the description proceeds.

In accordance with the present invention, a tamper indicating device is provided for connection to an injection site having a main body portion, a first inlet, a second inlet including a pierceable, self-sealing member, an outlet, and with the first inlet, second inlet and outlet being in fluid communication with the main body portion. The tamper indicating device comprises a cap covering the second inlet and rendering the pierceable, self-sealing member inaccessible. The cap comprises a first portion for connection to the second inlet and a second portion separated from the first portion by a frangible section. A handle extends from the second portion and is operable when actuated to break the second portion away from the first portion at the frangible section. In this manner, the pierceable, self-sealing member becomes accessible while the first portion remains connected to the second inlet.

In the illustrative embodiment, the first portion comprises a ring member substantially encircling the second inlet. The second portion comprises a cup-shaped member and the frangible section comprises an annular thin section coupling the first portion to the second portion. The tamper indicating means has a color that is different from the color of the second inlet so that when the second portion is broken away from the first portion, the color of the first portion which remains connected to the second inlet will contrast with the color of the second inlet, to show that the injection site had a tamper indicating device that has been partially removed.

A more detailed explanation of the invention is provided in the following description and claims, and is illustrated in the accompanying drawings.

DETAILED DESCRIPTION OF THE ILLUSTRATIVE EMBODIMENT

Figure 1:
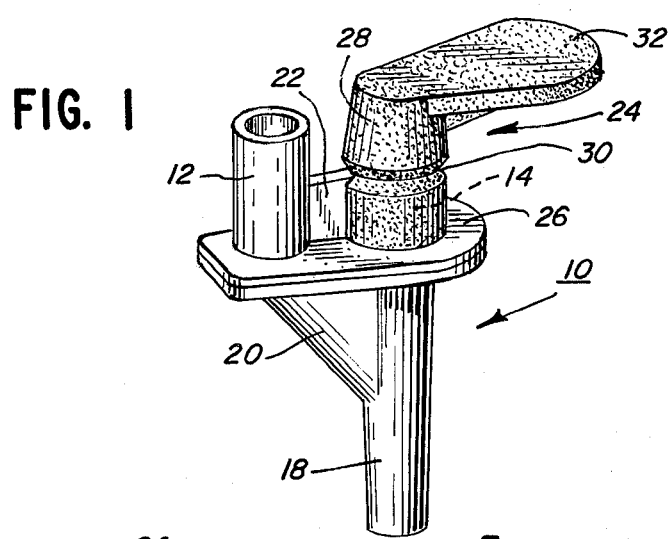
FIG. 1 is a perspective view of an injection site with tamper indicating means, constructed in accordance with the principles of the present invention.
Figure 2:
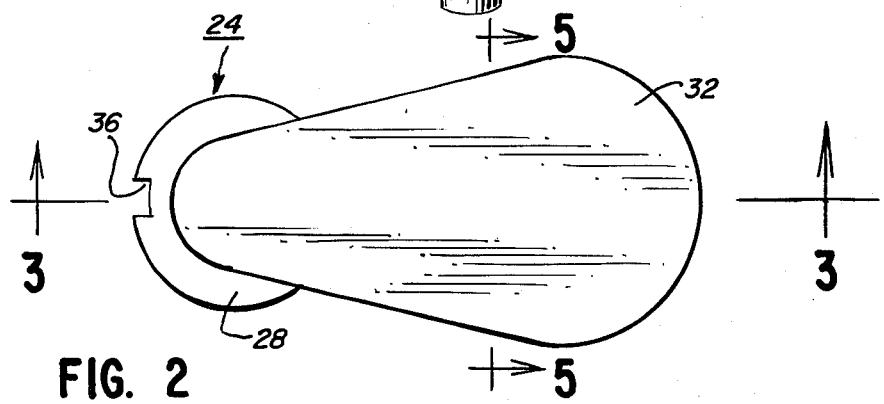
FIG. 2 is a top plan view of a tamper indicating device constructed in accordance with the principles of the present invention.
Figure 6:
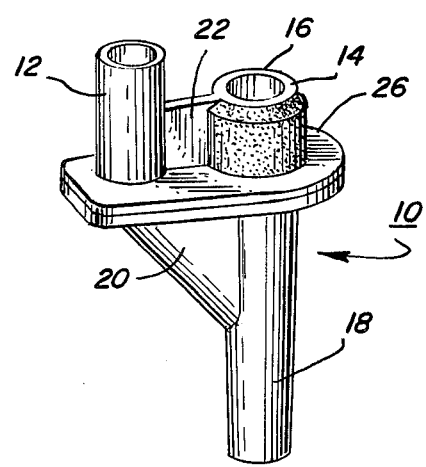
FIG. 6 is a perspective view of the injection site of FIG. 1, after a portion of the tamper indicating means has been removed.

Referring to FIGS. 1 and 6 in particular, the injection site 10 illustrated therein comprises a first inlet 12 for connection to a tube leading to a parenteral source of liquid, a second inlet 14 (FIG. 6) having a pierceable self-sealing diaphragm located therein as is well-known in the art, an outlet 18 for coupling to tubing which is connected to a patient, a main body portion 20 with which inlets 12 and 14 and outlet 18 communicate, and a ridge 22 connecting inlets 12 and 14 to aid in preventing tubing from becoming caught between these inlets. Such an injection site is illustrated in a pending U.S. patent application in the name of Herbert Mittleman, Ser. No. 892,766, filed Apr. 3, 1978. Referring to FIG. 6, it can be seen that the top plane of pierceable diaphragm 16 is generally coplanar with the top of second inlet 14.

Inlet 14 is substantially encircled and covered by tamper indicating device 24. Tamper indicating device 24 is formed in a one-piece integral molded construction, and comprises a first portion 26, which is cylindrical with its internal wall being solvent bonded to the external wall of second inlet 14, a second portion 28 which is generally cup-shaped and is separated from first portion 26 by a frangible section 30, and a handle 32 which is a generally flat member extending perpendicular to the axis of cup-shaped second portion 28 (and thus perpendicular to the axis of second inlet 14).

Figure 3:
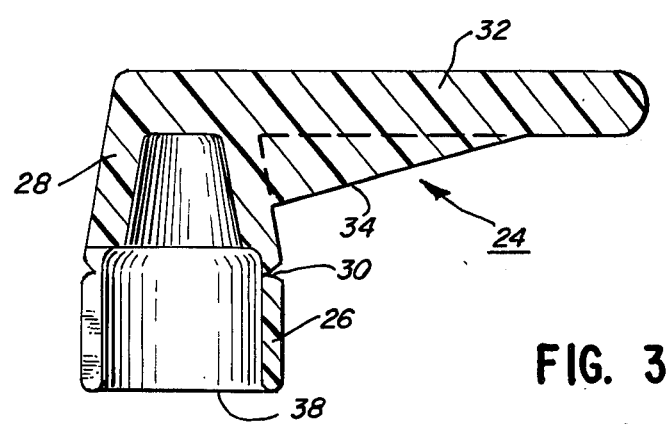
FIG. 3 is a cross-sectional elevation thereof, taken along the plane of the line 3—3 of FIG. 2.

Frangible section 30 comprises an annular thin section, as most clearly illustrated in FIG. 3, with frangible section 30 being in general alignment with the top of second inlet 14. For rigidity purposes, i.e., in order to prevent handle 32 from breaking away from second portion 28, a gusset 34 bridging the underside of handle 32 and a side of second portion 28 is provided.

Figure 4:
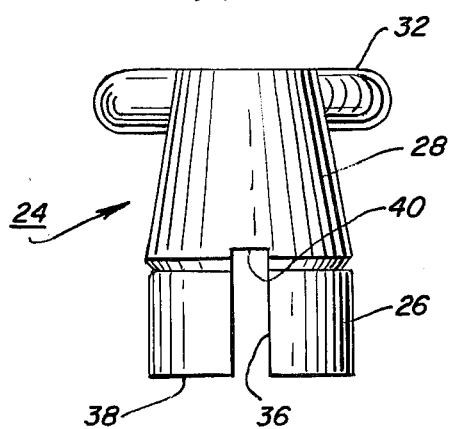
FIG. 4 is a left side elevation of the tamper indicating device of FIG. 2.
Figure 5:
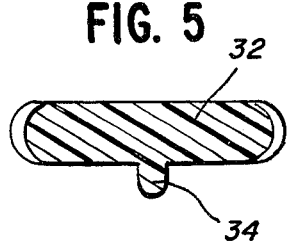
FIG. 5 is a cross-sectional elevation taken along the plane of the line 5—5 of FIG. 2.

One side of tamper indicating device 24 defines a rectangular slot 36 (FIG. 4) which extends from the bottom 38 of first portion 26 to a level just above the frangible section 30. This slot 36 is of a width to accommodate ridge 22, whereby the first portion 26 will encircle second inlet 14 except for ridge 22. Slot 36 is such that its top wall 40 is above the plane of the top of inlet 14, thereby providing a small opening so that inlet 14 can be ethylene trioxide sterilized notwithstanding the presence of tamper indicating device 24 thereon.

With reference to FIGS. 1 and 6, it can be seen that when tamper indicating device 24 is on second inlet 14, pierceable diaphragm 16 is inaccessible. In order for pierceable diaphragm 16 to become accessible, handle 32 is lifted upwardly to break the frangible section 30 so that second portion 28 can be removed from first portion 26. When second portion 28 is removed, the first portion 26 will remain attached to second inlet 14 as illustrated in FIG. 6.

The tamper indicating device 24 is formed of a plastic having a different color than the color of second inlet 14, so that once handle 32 and second portion 28 are removed, an operator can readily see that a portion of the tamper indicating device 24 has been removed. As an example, although no limitation is intended, the tamper indicating device 24 may be a bright color, such as red, while second inlet 14 may be white.

Although an illustrative embodiment of the invention has been shown and described, it is to be understood that various modifications and substitutions may be made by those skilled in the art without departing from the novel spirit and scope of the present invention.

That which is claimed is:

1. An injection site having a main body portion, a first inlet, a second inlet including a pierceable self-sealing member, and an outlet, the first inlet, second inlet and outlet being in fluid communication with the main body portion, the improvement comprising:

tamper indicating means connected to said second inlet, said tamper indicating means comprising a cap covering said second inlet and rendering said pierceable self-sealing member inaccessible, said cap comprising a first portion connected to said second inlet and a second portion separated from said first portion by a frangible section, a handle extending from said second portion and operable when actuated to break the second portion away from the first portion at said frangible section, with the first portion remaining connected to said second inlet and with the pierceable self-sealing member being accessible; said first portion comprising a ring member substantially encircling said second inlet, said second portion comprising a cup-shaped member and said frangible section comprising an annular thin section coupling said first portion to said second portion;

said second portion defining an opening adjacent said frangible section, said opening being defined in part by a wall which is above the plane of the top of said second inlet for enabling gas sterilization.

2. An injection site as described in claim 1, wherein said first portion has a different color from the color of said second inlet.

3. An injection site as described in claim 1, wherein said tamper indicating means is formed in an integral one-piece molded construction.

* * * * *